United States Patent [19]

Ruigt et al.

[11] Patent Number: 5,430,063
[45] Date of Patent: Jul. 4, 1995

[54] PHENOXYPHENYL DERIVATIVES, COMPOSITIONS THEREOF AND METHODS FOR THEIR USE

[75] Inventors: Gerardus S. F. Ruigt, Oss, Netherlands; Dirk Leysen, Lommel, Belgium; Johannes H. Wieringa, Heesch, Netherlands

[73] Assignee: Akzo N.V., Velperweg, Netherlands

[21] Appl. No.: 12,700

[22] Filed: Feb. 3, 1993

Related U.S. Application Data

[62] Division of Ser. No. 891,545, May 29, 1992, Pat. No. 5,190,965.

[30] Foreign Application Priority Data

May 29, 1991 [EP] European Pat. Off. ........... 91201288

[51] Int. Cl.$^6$ .................. A61K 31/135; C07C 217/26; C07C 233/56
[52] U.S. Cl. ..................................... 514/650; 514/401; 564/182; 564/347; 564/348; 564/350; 564/355; 564/387; 564/389; 564/390
[58] Field of Search ............... 564/182, 355, 430, 347, 564/348, 387, 389, 390; 514/401, 650

[56] References Cited

U.S. PATENT DOCUMENTS

| | | | |
|---|---|---|---|
| 3,579,582 | 5/1971 | Symon | 564/387 X |
| 3,946,119 | 3/1976 | Kathawala | 564/389 X |
| 3,996,278 | 12/1976 | Schlager | 564/389 X |
| 3,996,279 | 12/1976 | Schlager | 564/389 X |
| 4,006,243 | 2/1977 | Strehlke et al. | 514/401 |
| 4,024,274 | 5/1977 | Druckrey et al. | 564/389 X |
| 4,055,665 | 10/1977 | Christy | 514/655 |
| 4,151,302 | 4/1979 | Gante et al. | 564/355 X |
| 4,161,529 | 7/1979 | Beregi et al. | 514/401 |
| 4,484,942 | 11/1984 | Kirino et al. | 564/182 X |
| 4,627,874 | 12/1986 | Takematsu et al. | 564/182 X |
| 5,134,168 | 7/1992 | Bitonti et al. | 514/655 |
| 5,149,714 | 9/1992 | Freedman | 564/355 X |
| 5,190,965 | 3/1993 | Ruigi et al. | 514/401 |

FOREIGN PATENT DOCUMENTS

| | | | |
|---|---|---|---|
| 2047677 | 4/1971 | Germany | 514/401 |
| 2-129161 | 5/1990 | Japan | 564/182 |
| 2-138159 | 5/1990 | Japan | 564/182 |
| 1187200 | 4/1970 | United Kingdom | 514/401 |

OTHER PUBLICATIONS

J. Jilek, "Potential Antidepresants: 2-(Phenylthio)Aralkylamines," Collection of Czechoslovak Chemical Communications, vol. 54, No. 7 pp. 1995–2008, Prague CS3 (1989).

Jilek et al, Collection of Czech. Chem. Comms, vol. 54, No. 7, pp. 1995–2008 Feb. (1989).

Remy, Chemical Abstracts, vol. 74, #141251x Feb. (1971).

Primary Examiner—Floyd D. Higel
Attorney, Agent, or Firm—Mary E. Gormley; William M. Blackstone

[57] ABSTRACT

The invention concerns a phenoxyphenyl compound having the formula

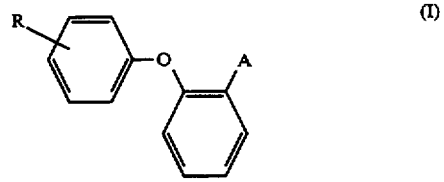

(I)

wherein
R is one or two halogen atoms; and
A is $CH_2NR_1R_2$ or 4,5-dihydro-1H-imidazole, in which $R_1$ and $R_2$ are independently selected from hydrogen and lower alkyl; or
a pharmaceutically acceptable salt thereof.

The compounds have long half-lives and can be used against depression.

9 Claims, No Drawings

PHENOXYPHENYL DERIVATIVES, COMPOSITIONS THEREOF AND METHODS FOR THEIR USE

This is a division of application Ser. No. 07/891,545 filed May 29, 1992 now U.S. Pat. No. 5,190,965.

The invention concerns phenoxyphenyl derivatives, their preparation, pharmaceutical preparations containing the same, and their use for the preparation of a medicament.

Derivatives having chemical structures related to the phenoxyphenyl derivatives of this invention are known from J. Jilek et al., Collect. Czech. Commun., 54, 1995 (1989), from J. Jilek et al., ibid, 54, 3294 (1989), from Czech Patent Application 151,755, and from European Patent Application 402,097. These references disclose phenylthiophenyl derivatives being selective serotonin reuptake inhibitors. It was found that these prior art compounds have short half-lives, which is a serious drawback in their practical use. The compounds of the present invention, however, have long half-lives and, apart from inhibition of the reuptake of serotonin, also inhibit the reuptake of noradrenaline and dopamine. The dopamine reuptake inhibition is thought to produce a fast elevation of mood, which makes the compounds suitable for the acute relief of symptoms in depression. This is considered to be a substantial advantage over known antidepressant drugs, like specific serotonin reuptake blockers, which have a delayed onset of action of two weeks or more. Moreover, the present compounds, because of their dopamine reuptake blocking properties, are less sedative than the prior art compounds, and thus more appropriate in the treatment of depressive patients with psychomotor retardation. The compounds of the invention can also be used to treat Parkinsons disease, obesity, anxiety disorders, central pain, addiction, and negative symptoms in schizophrenic patients.

The phenoxyphenyl derivatives of this invention have the formula

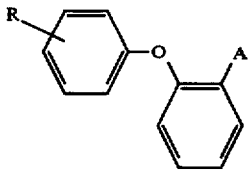

(I)

wherein

R is one or two halogen atoms; and

A is $CH_2NR_1R_2$ or 4,5-dihydro-1H-imidazole, in which $R_1$ and $R_2$ are independently selected from hydrogen and lower alkyl; or a pharmaceutically acceptable salt thereof.

Preferred compounds according to this invention are phenoxyphenyl derivatives according to formula I, wherein R is one or two chlorine atoms, or a pharmaceutically acceptable salt thereof.

The phenoxyphenyl derivatives of formula I, wherein A is $CH_2NH_2$, $CH_2N(CH_3)_2$, or 4,5-dihydro-1H-imidazole, and preferably wherein, moreover, R is one or two chlorine substituents, or a pharmaceutically acceptable salt thereof, are even more preferred.

The most preferred phenoxyphenyl derivatives are 2-(3,4-dichlorophenoxy)benzenemethanamine and 2-[2-(4-chloro-phenoxy)phenyl]-4,5-dihydro-1H-imidazole, or pharmaceutically acceptable salts thereof.

The term lower alkyl, used in the definition of the phenoxyphenyl derivatives having formula I, means a branched or unbranched alkyl group having preferably 1–6 carbon atoms, such as methyl, ethyl, propyl, isopropyl, butyl, tert-butyl, pentyl, hexyl and the like. Preferred alkyl groups have 1–4 carbon atoms, and most preferred is the methyl group.

The term halogen used in the definition of formula I means fluorine, chlorine, bromine or iodine. Chlorine is the preferred halogen.

The novel compounds of formula I may be isolated from a reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, pamoic acid, or ascorbic acid.

The phenoxyphenyl derivatives according to this invention can be prepared by methods known for analogous compounds.

A suitable method of preparation is a condensation of a nitrile having the formula

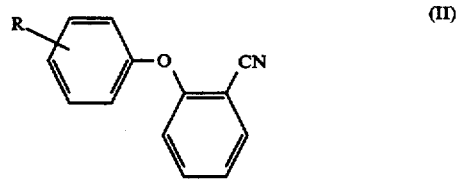

(II)

wherein R has the previously given meaning, with 1,2-ethanediamine, optionally followed by conversion into a pharmaceutically acceptable salt; or a reduction of the nitrile having formula II, optionally followed by alkylation and/or conversion into a pharmaceutically acceptable salt.

The nitrile having formula II can be prepared by condensation of 2-halobenzonitrile, and preferably 2-bromobenzonitrile, with a mono- or dihalo substituted phenol under alkaline conditions. The nitrile may also be prepared by condensation of 2-hydroxybenzonitrile and a bis[mono- or dihalobenzene] iodonium salt, which can be obtained from mono- or dihalobenzene, iodine, and a mixture of sulfuric and nitric acid.

The phenoxyphenyl derivative of formula I having A is $CH_2NR_1R_2$, wherein $R_1$ and $R_2$ have the previously given meanings, can also be prepared by reduction of an amide having formula

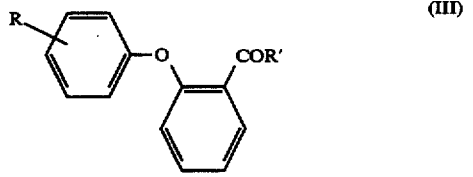

(III)

wherein R has the previously given meaning, and R' is $NR_1R_2$, in which $R_1$ and $R_2$ have the previously given meanings.

Compounds of formula I having A is 4,5-dihydro-1H-imidazole can also be prepared from a nitrile having formula II through a Pinner reaction giving an imino ester, which can be converted into the 4,5-dihydro-1H-imidazole by 1,2-ethanediamine.

Condensation of 1,2-ethanediamine with acids or esters having formula III, wherein R has the previously given meaning and R' is hydroxy, or methoxy or another lower alkoxy, also gives the desired phenoxyphenyl derivative having A is 4,5-dihydro-1H-imidazole. Lower alkoxy means an alkoxy group of which the alkyl moiety is a lower alkyl group as previously defined.

Phenoxyphenyl derivatives of formula I having A is $CH_2NR_1R_2$ can be prepared from acids or esters of formula III by reduction to the corresponding alcohol, conversion of the hydroxy group into a suitable leaving group, such as chlorine or bromine, and condensation with an amine having the formula $HNR_1R_2$, wherein $R_1$ and $R_2$ have the previously given meanings.

It is possible to convert the products obtained by one of the previously mentioned procedures into another product according to the invention. Using generally known methods it is, for instance, possible to convert compounds wherein $R_1$ and/or $R_2$ is hydrogen, e.g. by a Leuckart-Wallach reaction, into compounds wherein $R_1$ and/or $R_2$ is alkyl.

The compounds of the invention may be administered enterally or parenterally, and for humans preferably in a daily dosage of 0.001–10 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

EXAMPLE 1

2-(4-chlorophenoxy)benzenemethanamine hydrochloride

A solution of 51.4 g of 4-chlorophenol in 500 ml of dry N,N-dimethylformamide (DMF) was added to a suspension of 20 g of 60% sodium hydride in 800 ml of dry DMF under nitrogen. After 30 min at 25° C., 1 g of 18-crown-6 was added. After the addition of 73 g of 2-bromobenzonitrile in 500 ml of dry DMF, the mixture was heated at 100° C. for 16 h. After concentration in vacuo, 2N sodium hydroxide and ethyl acetate were added. The organic layer was separated, washed with 2N sodium hydroxide and water, dried over magnesium sulfate, and evaporated to dryness. The residue was recrystallized from methanol to give in 60% yield 2-(4-chlorophenoxy)benzonitrile. To a suspension of 6 g of lithium aluminum hydride in 100 ml of dry tetrahydrofuran (THF) were added under nitrogen 20 g of 2-(4-chlorophenoxy)benzonitrile. The mixture was heated at reflux for 3 h, cooled, and 25 ml of 1N sodium hydroxide were added dropwise. The precipitate formed was filtered off and washed with diethyl ether. The filtrate was evaporated to dryness, dissolved in ethyl acetate and acidified with a saturated solution of hydrochloric acid in ethanol. The precipitate was collected and recrystallized from ethanol to give in 95% yield 2-(4-chlorophenoxy)benzenemethanamine hydrochloride. mp 253° C.

EXAMPLE 2

2-(3,4-dichlorophenoxy)benzenemethanamine hydrochloride

To a vigorously stirred solution of 12.7 g of iodine in 13 ml of 60% fuming sulfuric acid and 33 ml of concentrated sulfuric acid, was added dropwise a solution of 7.5 ml of 90% fuming nitric acid, 1.9 ml of 60% fuming sulfuric acid, and 5.5 ml of concentrated sulfuric acid. The mixture was stirred for 2 h at 70°–80° C. After cooling to 0° C., a solution of 28.2 ml of 1,2-dichlorobenzene was added under vigorous stirring. The reaction mixture was kept at 45° C. for 2 h, cooled to 0° C., and 100 ml of cold water were added at once. The aqueous layer was decanted, the residue, dissolved in methanol, and 5 ml of concentrated hydrochloric acid were added. The precipitate, after filtration and washing with methanol, was dried, and 24.4 g of this precipitate were added to a solution of 5.6 g of 2-hydroxybenzonitrile and 2.2 g of sodium hydroxide in 440 ml of water. After 22 h of reflux, the mixture was cooled and extracted with diethyl ether. The organic layer was washed with 2N sodium hydroxide, dried over magnesium sulfate, and evaporated to dryness. The residue was recrystallized from diethyl ether to give in 80% yield 2-(3,4-dichlorophenoxy)benzonitrile.

A solution of 10 g of anhydrous aluminum chloride in 150 ml of dry diethyl ether was added dropwise under nitrogen to a suspension of 3.1 g of lithium aluminum hydride in 150 ml of dry diethyl ether, and the mixture was cooled at 0° C. After 30 min at 0° C., a solution of 5.0 g of 2-(3,4-dichlorophenoxy)benzonitrile in 150 ml of dry diethyl ether was added slowly. The mixture was stirred for 24 h at 25° C., and a concentrated aqueous solution of sodium hydrogen carbonate was added. The precipitate was filtered off, the filtrate was evaporated to dryness, dissolved in ethyl acetate, and acidified with a concentrated solution of hydrochloric acid in ethanol. The precipitate was collected and recrystallized from a mixture of ethanol and diethyl ether, to give in 75% yield 2-(3,4-dichlorophenoxy)benzenemethanamine hydrochloride. mp 213° C.

EXAMPLE 3

By addition of an aqueous solution of the disodium salt of pamoic acid to a solution of the compound of example 2 in ethanol, was prepared 2-(3,4-dichlorophenoxy)benzenemethanamine 4,4'-methylenebis[3-hydroxy-2-naphthalenecarboxylic acid] (2:1) salt. mp 230° C.

EXAMPLE 4

2-(4-chlorophenoxy)-N,N-dimethylbenzenemethanamine (Z)-2-butenedioate

A mixture of 5 g of 2-(4-chlorophenoxy)benzenemethanamine (Example 1), 50 ml of formic acid, and 50 ml of a 37% solution of formaldehyde in water was heated at 100° C. for 3 h. The solution was cooled, made alkaline with sodium hydroxide, and extracted with dichloromethane. The organic layer was washed with brine, dried over magnesium sulfate, and evaporated to dryness. The residue was dissolved in ethanol and maleic acid was added. After dilution with diethyl ether, the precipitate was collected, washed with diethyl ether and dried, to give in 80% yield 2-(4-chlorophenoxy)-

N,N-dimethylbenzenemethanamine (Z)-2-butenedioate. mp 118° C.

EXAMPLE 5

2-[2-(4-chlorophenoxy)phenyl]-4,5-dihydro-1H-imidazole (Z)-2-butenedioate

A solution of 20 g of 2-(4-chlorophenoxy)benzonitrile (Example 1) in 80 ml of 1,2-ethanediamine was saturated with hydrogen sulfide during 30 min at 0° C. The mixture was stirred at 25° C. for 4 days, concentrated, and ethyl acetate was added. The organic layer was washed with 2N sodium hydroxide, dried over magnesium sulfate, and evaporated to dryness. The residue was dissolved in ethanol, treated with maleic acid, and recrystallized from ethanol to give in 80% yield 2-[2-(4-chloro-phenoxy)phenyl]-4,5-dihydro-1H-imidazole (Z)-2-butenedioate. mp 207° C.

EXAMPLE 6

In an analogous manner, as described in Example 5, were prepared:

a.  2-[2-(3,4-dichlorophenoxy)phenyl]-4,5-dihydro-1H-imidazole (Z)-2-butenedioate. mp 123° C.

b.  2-[2-(4-chlorophenoxy)phenyl]-4,5-dihydro-1H-imidazole  4,4'-methylenebis[3-hydroxy-2-naphthalenecarboxylic acid] (2:1) salt. mp >250° C.

EXAMPLE 7

The biological half-lives of the phenoxyphenyl derivatives were determined for the sleep-wake behaviour in rats and compared with the half-lives of the prior art compounds.

| Product of Example | half-life in h |
| --- | --- |
| 1 | 1–2.5 |
| 2 | 2.5 |
| 4 | 1 |
| 5 | 3 |
| 6a. | 1.5–2.5 |
| prior art: | |
| 2-(phenylthio)benzenemethanamine | 0.5 |
| 2-[(4-methoxyphenyl)thio]-benzenemethanamine | <0.5 |

We claim:

1. A phenoxyphenyl derivative having the formula

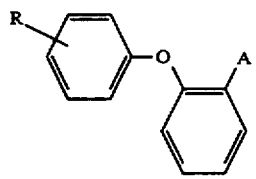

(I)

wherein
R is one or two halogen atoms; and
A is $CH_2NR_1R_2$, in which
$R_1$ and $R_2$ are independently selected from hydrogen and lower alkyl; or
a pharmaceutically acceptable salt thereof.

2. The phenoxyphenyl derivative of claim 1, wherein R is one or two chlorine atoms, or a pharmaceutically acceptable salt thereof.

3. The phenoxyphenyl derivative of claim 1, wherein A is $CH_2NH_2$, $CH_2N(CH_3)_2$ or a pharmaceutically acceptable salt thereof.

4. 2-(3,4-dichlorophenoxy)benzenemethanamine or a pharmaceutically acceptable salt thereof.

5. A pharmaceutical preparation containing the phenoxyphenyl derivative of claim 1 in admixture with pharmaceutically acceptable auxiliaries.

6. A method of inhibiting the reuptake of dopamine, comprising administering a physiologically effective amount of a phenoxyphenyl derivative having the formula

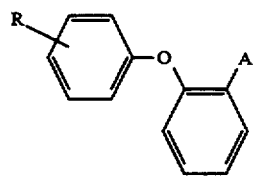

(I)

wherein
R is one or two halogen atoms; and
A is $CH_2NR_1R_2$, in which $R_1$ and $R_2$ are independently selected from hydrogen and lower alkyl; or
a pharmaceutically acceptable salt thereof.

7. The method of claim 6, wherein R is one or two chlorine atoms, or a pharmaceutically acceptable salt thereof.

8. The method of claim 6, wherein A is $CH_2NH_2$, $CH_2N(CH_3)_2$ or a pharmaceutically acceptable salt thereof.

9. The method of claim 6, wherein the phenoxyphenyl derivative is 2-(3,4-dichlorophenoxy)benzenemethanamine or a pharmaceutically acceptable salt thereof.

* * * * *